ns Patent [19]

Sato

[11] Patent Number: 4,596,577
[45] Date of Patent: Jun. 24, 1986

[54] NAPPED FLUORORESIN MATERIALS HAVING CONTINUOUS PORES, AND A METHOD OF MANUFACTURING THE SAME

[75] Inventor: Toshikazu Sato, Irumagun, Japan
[73] Assignee: Junkosha Co. Ltd., Tokyo, Japan
[21] Appl. No.: 370,563
[22] Filed: Apr. 21, 1982
[51] Int. Cl.[4] .................................................. A61F 1/00
[52] U.S. Cl. ......................................... 623/1; 128/1 R
[58] Field of Search .................. 3/1, 1.4; 264/41, 210, 264/501, 127, 154; 428/376; 427/2; 128/334 R, 1 R

[56] References Cited
U.S. PATENT DOCUMENTS
4,290,987 9/1981 Soehngen et al. ..................... 264/41

FOREIGN PATENT DOCUMENTS
2902434 8/1979 Fed. Rep. of Germany ........... 3/1.4

Primary Examiner—Richard J. Apley
Assistant Examiner—David J. Isabella
Attorney, Agent, or Firm—Mortenson & Uebler

[57] ABSTRACT

A sheet or tube of fluororesin material having continuous pores, particularly polytetrafluoroethylene, has a nap raised on at least one surface thereof, and is suitable for prosthetic use as a patch, or an artificial blood vessel. A method of manufacturing such napped fluororesin material comprises impregnating fluororesin material having continuous pores with water, freezing it, raising a nap thereon, and defrosting and dewatering it.

4 Claims, 4 Drawing Figures

NAPPED FLUORORESIN MATERIALS HAVING CONTINUOUS PORES, AND A METHOD OF MANUFACTURING THE SAME

BACKGROUND OF THE INVENTION

1. Field of the Invention

This invention relates to napped fluororesin materials having continuous pores, and which are used for the prosthesis of a damaged heart or other organs, or blood vessels, or the manufacture of filters, clothes, or the like.

2. Description of the Prior Art

Sheets or tubes of fluororesins having continuous pores, particularly polytetrafluoroethylene (PTFE), are widely used for making patches, artificial blood vessels, or other medical substitutes, various types of filters, diaphragms, or water-repellent, air-permeable clothes. These products are all very effective. Such PTFE material having continuous pores can be made by a method as disclosed in U.S. Pat. No. 3,953,566. According to this method, an admixture of fine PTFE powder and a liquid lubricant is preformed into a paste, the paste is extruded through a ram extruder, and the extruded product is stretched in a selected direction at a stretch rate of at least 10% per second, or its original length in the stretched direction, at a temperature lower than the melting point of PTFE crystals (about 327° C.). If required, the material may be heated at a temperature higher than 327° C., while it is held against shrinkage, to provide a baked product. Products having different shapes and physical properties can be obtained if the shape of the product obtained by extrusion, the stretch ratio and the heating temperature are varied. These stretched porous PTFE products comprise numerous fine nodes interconnected by fibrils, and defining numerous fine continuous pores having a diameter of, say, 0.1 to 5 microns. The tubular products may be used individually or stacked together to provide artificial blood vessels, while the membrane products may be laminated on other material to make various types of filters or clothes, or the like.

None of the known products have, however, been satisfactory for all end uses. Some materials for prosthetic use comprise expanded PTFE alone, while others comprise a combination of expanded PTFE and other woven or knitted material, or plastic coating. They are available in tubular form for artificial blood vessels, and in sheet form for patches. The inner surface of the prosthetic material composed only of expanded PTFE, which is adapted to contact blood, is gradually covered after implantation with a false membrane spreading from the stitched region to form a structure which is comparable to the inner surface of a natural blood vessel in thrombosis resistance. The fibrils in a baked product are somewhat more likely to cause thrombosis than in an unbaked product. Both the baked and unbaked products have so smooth surfaces that the false membrane formed thereon is likely to peel away when some external impact has been applied thereto. If any such structure formed newly on the prosthetic material or any other matter adhering thereto peels away, the fragments thereof are likely to block finer blood vessels, resulting in serious thrombosis.

The outer surface of such prosthetic material, which is adapted to contact the body tissues, is also so smooth that no satisfactory adherence of the body tissues, or growth into the fine structure of the tissues takes place after implantation. Various kinds of prosthetic materials composed of expanded PTFE, and woven or knitted material have been proposed to improve the compatibility of expanded PTFE with the body tissues, and prevent the material from being torn by the stitching thread. These composite prosthetic materials are so reactive with the body tissues that they may cause thrombosis, or prevent the formation of a uniform false membrane. What is worse, serious thrombosis may result from the separation of fibers from the knitted material in the stitched region.

The smooth surface of expanded PTFE is difficult to dye. This is a great disadvantage of expanded PTFE for use as clothing material. It is not suitable for use as a facing for a laminate, but is mainly used to form an intermediate layer therein. A velvety surface would certainly give expanded PTFE a wider range of application in the field of clothing.

SUMMARY OF THE INVENTION

It is an object of this invention to provide fluororesin material having continuous pores, and which are free from any of the drawbacks of the prior art.

It is another object of this invention to provide a method of manufacturing any such fluororesin material.

According to this invention, there is, thus, provided fluororesin material having continuous pores, and which is at least partly napped. The material of this invention may be manufactured by a method which essentially comprises impregnating fluororesin material having continuous pores with water, freezing it, raising a nap on the frozen material, defrosting the napped material, and dewatering it.

The material of this invention provides, for example, a very useful medical membrane, or patch which can form a uniform false membrane thereon quickly without undergoing any antibody reaction with any adjacent organ, and which does not present any problem without separating any foreign matter even if the incision is left open for a prolonged time. If it is used in the manufacture of clothing, its surface provides a velvety handle. The material of this invention is also suitable for making filters, and for many other purposes. The method of this invention is of great industrial value, since it facilitates economical napping on the continuously porous fluororesin material which is usually poor in workability.

DETAILED DESCRIPTION OF THE INVENTION

Figure 1:
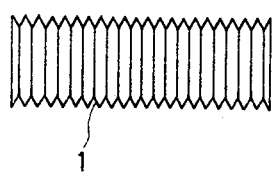
FIG. 1 is a fragmentary top plan view of an artificial blood vessel known in the art.

The prior art will be described more specifically with reference to FIG. 1 and FIG. 2 of the drawings before this invention is described in detail. Refering to FIG. 1, there is fragmentarily shown an artificial blood vessel 1 known in the art. The artificial blood vessel 1 comprises a tube of knitted fibers, and is stitched to a natural blood vessel. Although it is possible that a false membrane may grow about a core defined by the knitted fibers to form a relatively satisfactory new blood vessel, the leakage of blood is often likely to occur during the stitching operation to cause an infant having only a small quantity of blood to die. Even if it does not die, some fibers are often likely to get separated and enter the finer blood vessel, and block it, resulting in serious thrombosis. It has, therefore, been proposed recently to employ a membrane of continuously porous fluororesin material having high thrombosis resistance, or any such membrane having a surface reinforced with knitted fibers.

Figure 2:
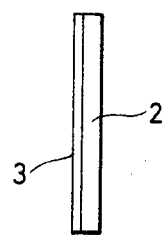
FIG. 2 is a side elevational view of a sheet of prosthetic material known in the art.

Such a membrane or sheet of prosthetic material known in the art is shown in FIG. 2. It comprises a membrane of fluororesin material having continuous pores 2, such as polytetrafluoroethylene, and a layer of knitted fibers 3 bonded closely to one surface of the membrane 2. The knitted fibers 3 reinforce the membrane 2, and also assists the formation of a false membrane about the area in which prosthesis is achieved. This prosthetic material is, however, also unsatisfactory, since some of the fibers are often likely to get separated and enter the heart or blood vessel, resulting in thrombosis, or other trouble. In order to overcome these disadvantages, it has been proposed to eliminate the kitted fibers 3, and employ a membrane composed solely of fluororesin material having a high degree of porosity and a very large pore diameter (i.e., a large fibril spacing). This attempt has, however, been unsuccessful, since a homogeneous membrane is difficult to manufacture, and the membrane does not permit fast growth in any uniform false membrane thereon.

According to this invention, a nap is raised on at least a portion of fluororesin material having continuous pores. The fluororesin material having continuous pores may, for example, comprise expanded PTFE obtained by stretching as hereinbefore described, a mixture thereof with a small quantity of other fluororesin, such as a copolymer of ethylene and tetrafluoroethylene, or tetrafluoroethylene and perfluoroalkylvinylether, porous material obtained by extracting an extractable powder from a mixture of fluororesin and the powder, or material obtained from fluororesin fibers by a papermaking process. The continuously porous fluororesin material obtained by stretching is most suitable. Such fluororesin material is too soft to be napped directly. It can, however, be napped economically, if it is impregnated with water, and frozen, and the frozen material is napped, defrosted and dewatered.

An unbaked sheet, tube or rod of polytetrafluoroethylene is prepared by a customary method, and stretched by a method as disclosed in U.S. Pat. No. 3,953,566, whereby it is formed with continuous pores. While it is held against shrinkage, it is baked, whereby its strength is increased, and any creep phenomenon is prevented. The fluororesin material having continuous pores is then impregnated with an alcohol having a low surface tension at ordinary room temperature. The alcohol is then, replaced with water. Instead of any such alcohol, an aqueous solution of a surface active agent may be used as a liquid assistant having a low surface tension for the impregnation of the material with water. Then, the material is placed in a freezer, and kept at a temperature which is sufficiently low to freeze the water, or usually in the range of −5° C. to −30° C. A nap can be raised on a surface of the frozen material if, for example, a rotary brush having relatively soft wires, such as of brass, is rubbed thereagainst. The frozen and napped material can be defrosted if it is either left to stand at ordinary room temperature, or placed in a drying oven having a temperature lower than the melting point of the fluororesin material and not causing any shrinkage thereof, or in the range of, say, 80° C. to 150° C. Then the material is dewatered and dried.

Figure 3:
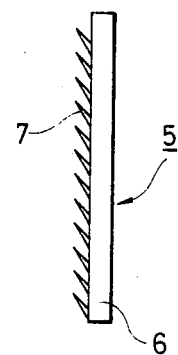
FIG. 3 is a side elevational view of a medical fluororesin membrane embodying this invention.

Referring now to FIG. 3, there is shown a prosthetic membrane 5 formed from the continuously porous fluororesin material prepared as hereinabove described. The membrane 5 comprises a sheet of continuous porous fluororesin material 6 having an outer surface on which a nap 7 is raised as hereinabove set forth. The nap 7 may usually be formed by fibrils from the original film, and partly torn material, and have a length in the range of, say, 0.5 to 1,000 microns, depending on the purpose for which the membrane 5 is used. As the nap 7 is raised uniformly on the outer surface of the fluororesin material 6, the prosthetic membrane 5 may be used successfully as, for example, a patch which does not undergo any antibody reaction with the human tissue, and forms a more uniform new tissue more quickly than the expanded PTFE material known in the art. The prosthetic membrane prepared from the napped material according to this invention remains highly stable until after its implantation.

Figure 4:
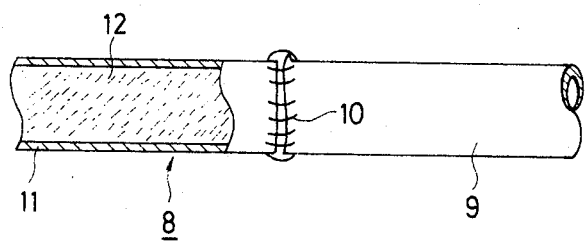
FIG. 4 is a fragmentary top plan view, partly in section, of a medical fluororesin tube embodying this invention, and stitched to a blood vessel.

FIG. 4 shows an artificial arterial tube 8 embodying this invention, and joined to a natural blood vessel 9 with a stitching thread 10. The artificial arterial tube 8 comprises a stretched and baked polytetrafluoroethylene tube 11 having an inner surface on which a nap 12 is uniformly formed. The nap can be provided on the outer surface of the tube 11, or both the inner and outer surfaces thereof. The nap 12 facilitates fast and uniform growth of a false membrane, and enables the artificial blood vessel to remain safe even if the incision is left open for a prolonged time.

Although the invention has been described with reference to the preferred embodiments thereof, it is to be understood that modifications or variations may be easily made by anybody of ordinary skill in the art without departing from the scope of this invention which is defined by the appended claims.

I claim:

1. A method of manufacturing a porous polytetrafluorothylene article having a microstructure of nodes interconnected by fibrils and a portion of at least one surface of which is napped comprising:
    (a) impregnating an expanded fluororesin article with a liquid solution;
    (b) lowering the temperature of said impregnated article below the freezing point of said liquid;
    (c) raising a nap on said impregnated article;
    (d) raising the temperature of said impregnated article above the freezing point of said liquid; and
    (e) removing said liquid.

2. The method of claim 1 in which said liquid is water.

3. The method of claim 2 in which said article is first impregnated with a liquid having a low surface tension and then impregnated by water, said water replacing said liquid with low surface tension prior to reducing said impregnated article below the melt point of the liquid.

4. The product produced by the process of claim 1, 2 or 3.

* * * * *